US005226878A

United States Patent [19]

Young

[11] Patent Number: 5,226,878

[45] Date of Patent: Jul. 13, 1993

[54] TWO-CONTAINER SYSTEM FOR MIXING MEDICAMENT WITH DILUENT INCLUDING SAFETY WAND TO PROTECT AGAINST IMPROPER TITRATION

[75] Inventor: J. Whitaker Young, Saint Michaels, Md.

[73] Assignee: Whitaker Designs, Inc., Saint Michaels, Md.

[21] Appl. No.: 818,889

[22] Filed: Jan. 10, 1992

[51] Int. Cl.$^5$ .......... A61M 37/00

[52] U.S. Cl. .......... 604/89; 604/82; 604/416; 604/903

[58] Field of Search .......... 604/82, 83, 85, 89, 604/91, 416, 903; 222/96, 97, 142.1, 142.7, 510

[56] References Cited

U.S. PATENT DOCUMENTS

| | | | |
|---|---|---|---|
| 2,721,552 | 10/1955 | Nosik . | |
| 2,764,157 | 9/1956 | Oliva et al. . | |
| 2,787,268 | 4/1957 | Greenspan . | |
| 3,670,728 | 6/1972 | Dabney | 604/91 |
| 3,858,580 | 1/1975 | Ogle | 604/91 |
| 4,467,588 | 8/1984 | Carveth . | |
| 4,583,971 | 4/1986 | Bocquet et al. . | |
| 4,610,684 | 9/1986 | Knox et al. . | |
| 4,781,679 | 11/1988 | Larkin . | |
| 4,784,658 | 11/1988 | Grabenkort . | |
| 4,871,354 | 10/1989 | Conn et al. | 604/89 |

FOREIGN PATENT DOCUMENTS

| | | | |
|---|---|---|---|
| 343075 | 2/1931 | United Kingdom | 604/416 |
| 8303539 | 10/1983 | World Int. Prop. O. | 604/85 |

*Primary Examiner*—C. Fred Rosenbaum
*Assistant Examiner*—C. Maglione

[57] ABSTRACT

An improved diluent container having a small elongated wand (made of plastic or similar material), designed to secure a drug vial cap in place and simultaneously obstruct an I.V. port in a diluent bag similar to an ADD-VANTAGE flexible diluent container. The device is actuated by grasping a gripper ball portion located approximately midway down the wand shaped plug from outside the I.V. bag and removing the vial cap end from the discharge opening between the vial, holding medicament, and the flexible diluent container. Once the vial capped end is removed, the medicament enters the diluent and is mixed by shaking or squeezing the flexible diluent container while maintaining the other end of the wand in the I.V. port. The device has a length which is designed so that the end of the wand shaped plug cannot be removed from the I.V. port of the flexible diluent container until the end blocking the drug vial has been removed from that opening. This thereby prevents the inadvertent administration of I.V. fluid without the medicament being thoroughly described and mixed in the fluid.

19 Claims, 2 Drawing Sheets

TWO-CONTAINER SYSTEM FOR MIXING MEDICAMENT WITH DILUENT INCLUDING SAFETY WAND TO PROTECT AGAINST IMPROPER TITRATION

FIELD OF THE INVENTION

The present application is directed to a dual container intravenous (I.V.) dispensing assembly in which an additive provided in an additive container is sterilely intermixed with diluent provided in a flexible diluent container. More particularly, the present invention is directed to a safety wand stopper for use in the above-described dual container system which ensures complete sterile intermixing of the contents of the two containers prior to dispensing.

BACKGROUND OF THE INVENTION

Several devices have been developed in the past for the intravenous administration of medicaments. Some such devices are shown in U.S. Pat. Nos. 4,467,588 to Carveth; 4,871,354 to Conn et al.; 4,583,971 to Bocquet et al.; and 4,784,658 to Grabenkort. One such container system known in the art is currently sold by Abbott Laboratories of North Chicago, Ill. under the trademark ADD-VANTAGE®. This system is discussed in the aforementioned U.S. Pat. No. 4,784,658 to Grabenkort (hereinafter the "Garbenkort Patent"), as well as U.S. Pat. Nos. 4,614,267 to Larkin and 4,614,515 to Tripp et. al. which patents are hereby incorporated by reference into the present application.

As shown in the Grabenkort Patent, two container systems have become widely accepted for administering medicaments stored in a liquid, powdered or crystalline form. Since it is imperative that the medicaments not be contaminated prior to usage, sealed glass vials are used to store the medicaments until joined with a diluent container.

In Grabenkort, the diluent is stored in a sealed flexible bag made of plastic or other pliable material. The diluent container has two separate outlets provided at opposing ends of the diluent container. The first outlet is specifically designed to receive the first or additive container (i.e., glass vial) in which the medicament is stored; the second outlet provides a channel for dispensing the mixture of diluent and medicament (I.V. fluid).

Two container systems are desirable for the intravenous (I.V.) administration of medicaments, particularly those medicaments which have a short shelf life when mixed with diluent. In use, the additive or medicament container is joined with the diluent container in preparation for depositing the medicament in the diluent.

Several methods have been used to effectuate this joining step without contaminating the contents of either container. In the Grabenkort Patent, once the medicament enters the second container, the diluent and medicament are mixed by squeezing or shaking the second container for a prescribed period of time or until the medicament is dissolved and evenly mixed with the diluent. After mixing, the two containers are suspended on a rack so as to urge the I.V. fluid toward the second channel. The second channel may then be connected to a system for delivering the mixture to an I.V. system.

Although conventional two container systems have been effective in preventing contamination of their contents, and allowing use of medicaments having a short shelf life when mixed with diluent, their design can not ensure that mixing of the I.V. solution is effected prior to dispensing. With such prior art systems it is possible to dispense diluent intravenously prior to admixture. Prior to mixture it is possible to dispense the diluent prior to any mixing of the medicament. In such a circumstance, when a substantial portion of the diluent is dispensed prior to admixture of the medicament with the diluent, once mixing is performed the concentration of medicament in the dispensed mixture may dramatically increase. For this reason, the above-mentioned prior art system is suitable only for the mixing and dispensing of relatively non-toxic medicaments where the medicament admixture is not critical. In fact the above-discussed prior art system is not considered satisfactory for the mixing and intravenous dispensing of relatively toxic medicaments such as chemotherapeutic agents, radiopharmaceuticals and antimicrobials. This is despite the fact that other attributes of the above-mentioned system, such as the complete isolation of the health care technician from the medicament, are ideal for use such toxic medicaments.

SUMMARY OF THE INVENTION

It is therefore an object and advantage of the present invention to provide a safety device for a two-container I.V. system that guards against the inadvertent administration of diluent prior to admixture of the medicament.

It is a further object of the present invention to ensure that the medicament will be properly titrated with diluent, thereby avoiding the dispensation of a higher than desired admixture of medicament.

It is a further object of the present invention to produce a two-container I.V. system which may be used with relatively toxic medicaments, which system will safely isolate the health care technician from the toxic medicament and will ensure that such a toxic medicament is properly titrated, thereby avoiding the attendant danger to the patient.

It is a further object and advantage of the present invention to accomplish the above mentioned objectives with a device that is easily manipulatable.

It is a still further object of the present invention is to prevent the inadvertent premature removal of a medicament container cap during transport and delivery thereby preventing the premature admixture of medicament and diluent.

BRIEF DESCRIPTION OF THE DRAWINGS

A better understanding of the invention will be had by reference to the embodiments illustrated in the drawings wherein.

DESCRIPTION OF PREFERRED EMBODIMENTS

Figure 1:
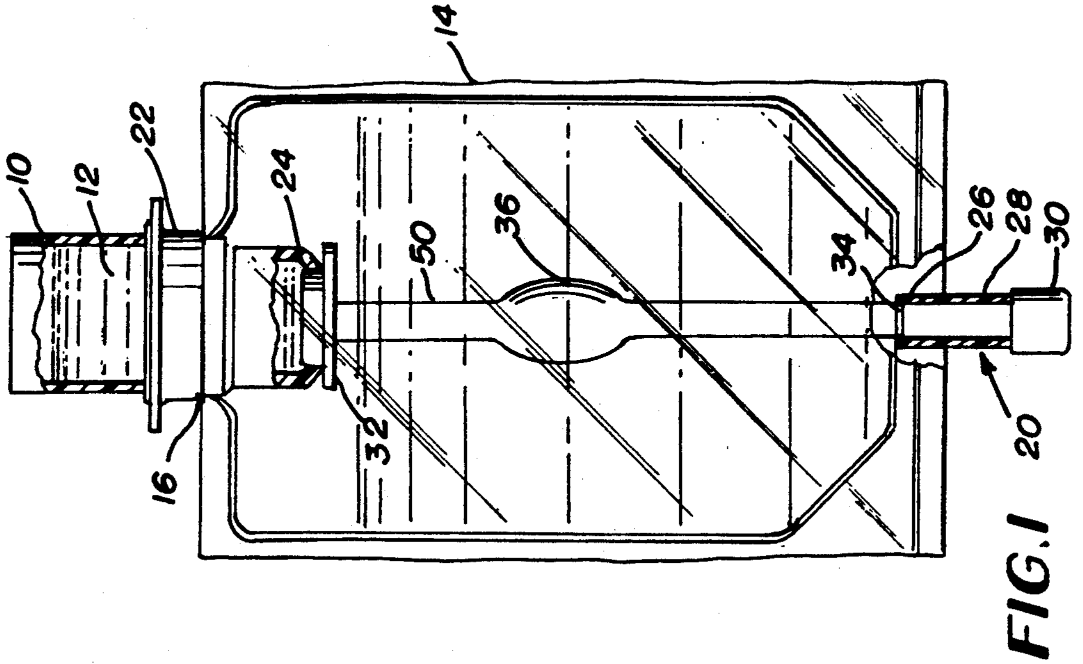
FIG. 1 is a front view of a two-container system showing a port plugging safety wand 50 in the transport and storage position.

FIG. 1 illustrates an arrangement of the essential components of the present invention as incorporated in a two-container system of the type disclosed in the Grabenkort Patent. A stopped medicament vial 10 holding medicament 12 is designed for engagement with a flexible diluent container 14 at a port 16.

The flexible diluent container 14 is provided with a first opening or medicament port 16 which is configured to receive the stopped medicament vial 10 and is further provided with a second opening or I.V. port 20 located at an opposed end of the container 14 from the medicament port 16. The medicament port 16 has a receiving port 22 for receiving the medicament vial 10 and a discharge opening 24 to allow communication of the contents of the stopped medicament vial 10 with the interior of the flexible diluent container 14.

The I.V. port 20 is positioned at the opposite end of the flexible diluent container 14 with respect to the medicament port 16 and used to dispense the mixed diluent and medicament from the flexible diluent container 14 once the I.V. is set and dispensing to the patient is begun. The I.V. port 20 includes an interior portion 26 and an exterior portion 28. A removable cap 30 covers the exterior portion 28 of the I.V. port 20 sealing the interior of the I.V. port from contamination and further sealing in the contents of the diluent container 14 until time for administration of the I.V. fluid.

According to the teachings of the present invention, a port plugging safety or stopper wand 50 is provided between the discharge opening 24 of medicament port 16 and the I.V. port 20, and at rest, provides an effective seal of both the medicament port 16 and the I.V. port plug 20. This port plugging safety wand replaces the port plug 50 of the Grabenkort Patent, performing substantially its same function and additionally performing the safety functions of the present invention. The port plugging safety wand 50 is of sufficient length so as to engage and block the discharge opening 24 of the medicament port 16 with a sealing member 32 while also inserting a plug end 34 of the wand 50 into and thereby effectively blocking the interior portion 26 of the I.V. port 20. The plug end 34 is conformably configured to the interior portion 26 of the I.V. port 20 to provide an effective seal therewith. The port plugging safety wand 50 is configured to extend into the interior portion 26 of the I.V. port 20 a sufficient distance so that the plug end 34 cannot be disengaged from the interior portion 26 of the I.V. port 20 without first moving the sealing stopper 32 to one side of the discharge opening 24, causing the medicament 12 within the stopped medicament vial 10 to enter the container 14.

The degree of extension of the plug end 34 into the inner portion of the I.V. port 20 may be selected by routine experimentation, but should be sufficient to prevent the health care technician from separating the plug end 34 of the port plugging safety wand 50 from the inner portion 26 of the I.V. port 20 and thus should be greater than the elastic extension of the flexible diluent container 14.

To aid in maneuvering of the port plugging safety wand 50, a gripper ball 36 is formed approximately halfway along the length thereof. The gripper ball 36 enables the health care technician to easily maneuver the port plugging safety wand 50 inside the flexible diluent container 14 to facilitate the admixture of the medicament 12 to form an I.V. solution to be dispensed. While a gripper ball is utilized in the preferred embodiment, any gripper means to facilitate extraction of the port plugging safety wand 50 from the I.V. port 20 and medicament port 16 may be utilized. However, the gripper means should have a thickness in at least one dimension no greater than the overall thickness of the dual container system of the present invention.

OPERATION

Figure 2:
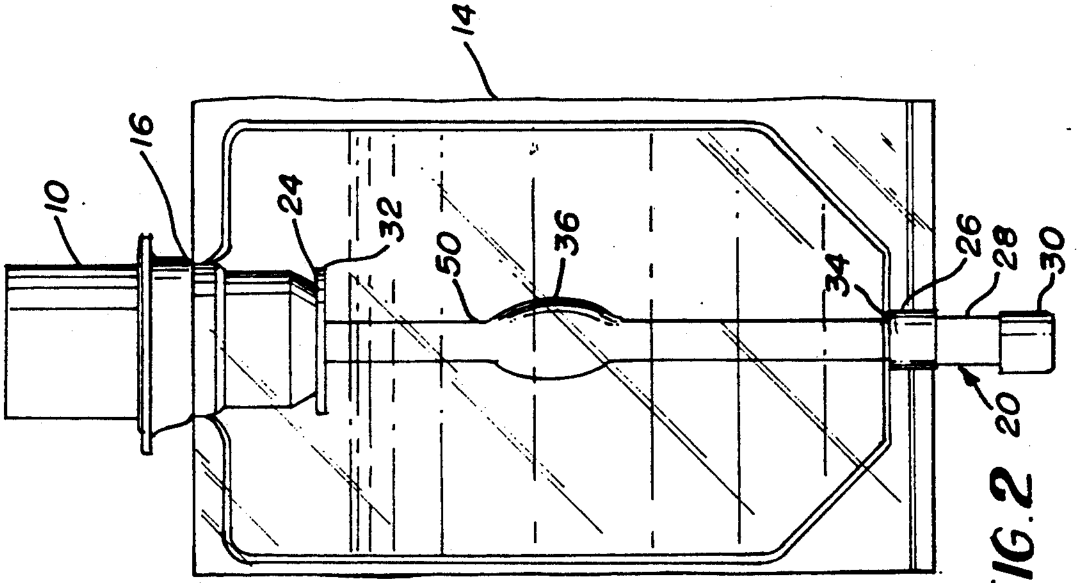
FIG. 2 shows a front view of a two-container system with the port plugging safety wand 50 in place.

The operation of the system of the present application will now be explained with reference to drawing FIGS. 2–5. In FIG. 2, the medicament vial 10 is engaged to the medicament port 16 of the flexible diluent container 14 in a manner explained in the Grabenkort Patent. The port plugging safety wand 50 is disposed between the interior portion 26 of the I.V. port 20 and the discharge opening 24 of the medicament port 16, both separating the medicament 12 from the diluent and preventing the dispensing of the diluent without prior admixture of the medicament.

Figure 3:
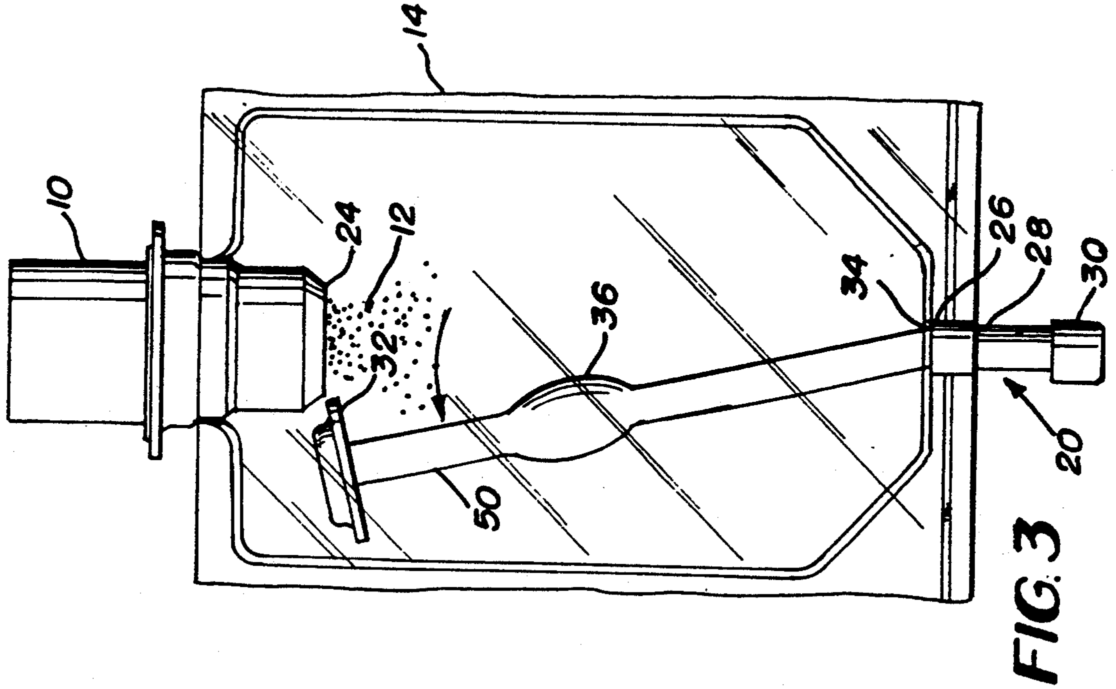
FIG. 3 shows a front view of the two-container system of FIG. 2 once the port plugging safety wand 50 is moved from the discharge opening 24 of the medicament port 16.

In FIG. 3, the first step in mixing the medicament with the dilution il illustrated. The port plugging safety wand 50 is designed to prevent removal from the I.V. port 20 without first moving the sealing stopper 32 away from the discharge opening 24 of the medicament port 16, allowing the medicament to enter the flexible diluent container 14.

By employing the relative flexibility of the diluent container 14 and grabbing the gripper ball 36 through the flexible diluent container 14, the sealing stopper 32 of the port plug safety wand 50 may be pulled away from the discharge opening axially with respect to the generally cylindrical medicament port 16 and then, subsequently, laterally displaced or is pushed aside to thereby clear the discharge opening 24. The medicament is thereafter free to exit the medicament vial 10 through the medicament port 16 and intermixes with the stored diluent. Because the port plugging safety wand 50 continues to block the I.V. port 20, undiluted medicament cannot enter the I.V. port 20 until after the medicament is supplied to the diluent container to facilitate mixture within the flexible diluent container 14. Accordingly, the system of the present invention cannot dispense anything whatsoever until mixture of medicament with diluent. Since no fluid flows from the system of the present invention, the health care technician will easily notice the error as no fluid will be delivered through the I.V. tubing set.

At this point, the medicament and diluent can be mixed by shaking or squeezing the diluent container 14. Due to the extension of the wand 50 into the interior portion 26 of the I.V. port 20, the port plugging safety wand 50 cannot be removed from the interior portion 26 of the I.V. port 20 until after the sealing stopper 32 of the wand 50 is removed from the medicament port 16, thereby preventing the diluent from being dispensed prior to mixture.

Figure 4:
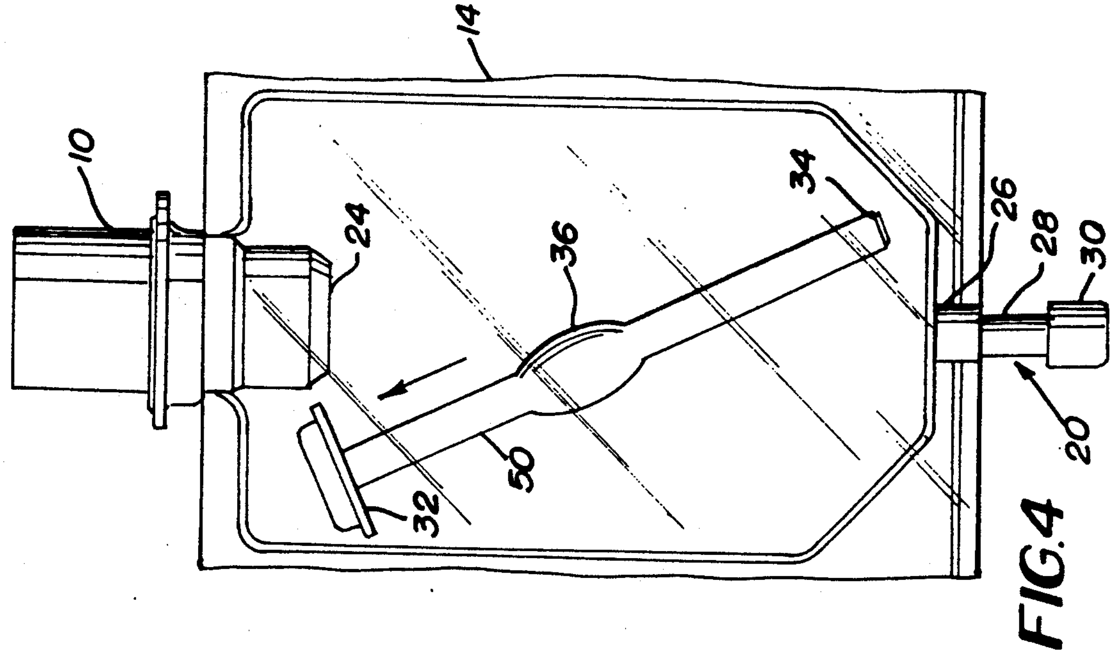
FIG. 4 shows a front view of the system of FIG. 2 once the diluent is mixed and the port plugging safety wand 50 is removed from the inner portion 26 of the I.V. port 20.

As FIG. 4 illustrates, once the mixing process has been completed the medication is ready to be dispensed through an I.V. tube or machine (not shown). Subsequent to the removal of the sealing stopper 32 from the discharge opening 24, the port plugging safety wand 50 can be easily removed from the I.V. port 20 by grasping the gripper ball 36 and extracting the plug end 34 of the port plugging safety wand 50 from the I.V. port 20.

Finally, the port plugging safety wand 50 rests in the interior of the diluent container 14 without obstructing the flow of I.V. fluid. The cap 30 is removed and the I.V. system is ready to dispense the thoroughly mixed medicament and diluent.

Activation of the drug delivery system including the mixing of the medicament and diluent by removal of the port plugging safety wand may be readily accomplished by the health care technician without the use of specially designed components or sophisticated methods which require an excessive number of procedures or prolonged exposure which might jeopardize sterility. Further, the drug delivery system of the present invention is suitable for use with toxic medicaments which require precise admixture to be safe and effective.

The above presented description of one embodiment of the invention will suggest a number of alternative embodiments to one of ordinary skill in the art. Such skilled persons will know that the invention is not necessarily restricted to the particular embodiments presented herein. The scope of the invention is defined solely by the terms of the following claims as given meaning by the preceding description.

I claim:

1. A two container dispensing system for dispensing an additive when mixed with a diluent comprising:
- an additive container containing an additive;
- a flexible diluent containing a diluent and having an additive port for communicating with the additive container and a dispensing port for dispensing mixed additive and diluent; and
- a stopper wand extending between said additive and dispensing ports and sealingly engaging both said ports, said stopper wand being removable from said dispensing port only after removal from said additive port to thereby ensure mixture of said additive and diluent prior to dispensing any diluent.

2. The system of claim 1 wherein said additive port and dispensing port are on opposed ends of said diluent container.

3. The system of claim 2 wherein said stopper wand includes a sealing stopper in sealing engagement with said additive port.

4. The system of claim 5 wherein said additive is a medicament and said dispensing system is an intravenous delivery system.

5. The diluent container of claim 1 wherein said additive container is insertable into said additive port of said diluent container for communication therewith.

6. A two container dispensing system for dispensing an additive when mixed with a diluent comprising:
- an additive container containing an additive;
- a flexible diluent container a diluent and having an additive port for communicating with the additive container and a dispensing port for dispensing mixed additive and diluent; and
- a stopper wand extending between said additive and dispensing ports and sealing engaging both said ports, said stopper wand being removable from said dispensing port only after removal from said additive port to thereby ensure mixture of said additive and diluent prior to dispensing any diluent, said stopper wand includes a sealing stopper in sealing engagement with said additive port;
- wherein said dispensing port has an interior surface;
- said stopper wand including a plug end comformably shaped to the interior surface of said dispensing port and extending into said dispensing port a distance sufficient to ensure that the plug end of said stopper wand may not be removed from said dispensing port prior to removal of said sealing stopper from said additive port.

7. The system of claim 5 wherein said additive is a medicament and said dispensing system is an intravenous delivery system.

8. A two container dispensing system for dispensing an additive when mixed with a diluent comprising;
- an additive container containing an additive;
- a diluent container containing a diluent and having an additive port for communicating with the additive container and a dispensing port for dispensing mixed additive and diluent; and
- a stopper wand extending between said additive and dispensing ports and sealing engaging both said ports, said stopper wand being removable from said dispensing port only after removal from said additive port to thereby ensure mixture of said additive and diluent prior to dispensing any diluent;
- wherein said additive container is insertable into said additive port of said diluent container for communication therewith.

9. A diluent container system for holding a diluent in a two-container system, the container system comprising:
- a sealed container for holding the diluent, said container having a medicament receiving port and a titrated medicament delivery port;
- said medicament receiving port defining a channel between a medicament container and the interior of said sealed container, said port having a first port end of sufficient width for receiving the medicament container, and a second port end located within the interior of said sealed container for communicating the content of the medicament container to the sealed container;
- said titrated medicament delivery port being positioned on said container opposite from said medicament receiving port in said sealed container, said titrated medicament delivery port having an interior end within the interior of said sealed container and an I.V. port end outside the sealed container for supplying titrated medicament for delivery to a patient; and
- an elongated wand with a first end and second end removably positioned within said container and extending between and blocking said medicament receiving and titrated medicament delivery ports, said wand being removably positioned so that only one port may be first opened.

10. The diluent container of claim 9 wherein said elongated wand must be removed from said medicament receiving port prior to removal from said titrated medicament delivery port.

11. The diluent container as recited in claim 9 wherein said first end of said elongated wand abuts said medicament receiving port.

12. The diluent container as recited in claim 9, wherein said second end of said elongated wand is inserted within said titrated medicament delivery port.

13. The diluent container as recited in claim 9, wherein said wand further comprises a sealing member positioned at said first end and sealing said medicament receiving port.

14. The diluent container as recited in claim 9, wherein said titrated medicament delivery port further comprises I.V. attachment means for attaching said container to an exterior I.V. apparatus.

15. A diluent container as recited in claim 9, further comprises removable cap means for sealing said titrated medicament delivery port.

16. The diluent container of claim 9 wherein said sealed container is flexible.

17. The diluent container as recited in claim 15, said wand further comprising a gripper means located between said first and second ends of said wand for assisting in moving said wand within the interior of said sealed container.

18. The diluent container as recited in claim 16, wherein said gripper means comprises an enlarged protuberance suitable for manipulation through said flexible sealed container.

19. The diluent container of claim 9 wherein said medicament container is insertable into said medicament receiving port of said diluent container system for communication therewith.

* * * * *